US009116253B2

(12) United States Patent
Stenzel et al.

(10) Patent No.: US 9,116,253 B2
(45) Date of Patent: Aug. 25, 2015

(54) SYSTEM AND METHOD FOR USING BIOCIDE COATING TO PREVENT MARINE GROWTH ON GEOPHYSICAL EQUIPMENT

(75) Inventors: Andre Stenzel, Sugar Land, TX (US); Bruce William Harrick, Cypress, TX (US); Steven Michael Roberts, Plymouth, MI (US)

(73) Assignee: PGS Geophysical AS, Oslo (NO)

( * ) Notice: Subject to any disclaimer, the term of this patent is extended or adjusted under 35 U.S.C. 154(b) by 905 days.

(21) Appl. No.: 13/343,560

(22) Filed: Jan. 4, 2012

(65) Prior Publication Data
US 2012/0176860 A1 Jul. 12, 2012

Related U.S. Application Data

(60) Provisional application No. 61/460,962, filed on Jan. 11, 2011.

(51) Int. Cl.
*G01V 1/20* (2006.01)
*C09D 5/16* (2006.01)
*A01N 59/16* (2006.01)

(52) U.S. Cl.
CPC .............. *G01V 1/201* (2013.01); *A01N 59/16* (2013.01); *C09D 5/16* (2013.01)

(58) Field of Classification Search
CPC .................. G01V 1/201; C09D 5/16–5/1693; A01N 59/16; A01N 59/00; C09J 175/00; C09J 175/04
See application file for complete search history.

(56) References Cited

U.S. PATENT DOCUMENTS

| | | | |
|---|---|---|---|
| 4,092,858 A | 6/1978 | Edgerton | |
| 4,175,161 A * | 11/1979 | Fogle et al. | ................. 428/424.2 |
| 4,751,113 A | 6/1988 | Riccio et al. | |
| 4,984,218 A | 1/1991 | Ritter et al. | |
| 5,228,005 A | 7/1993 | Bjelland | |
| 5,302,414 A | 4/1994 | Alkhimov et al. | |
| 5,532,980 A | 7/1996 | Zarate et al. | |
| 5,735,226 A | 4/1998 | McNeal | |
| 6,009,042 A | 12/1999 | Workman et al. | |
| 6,177,496 B1 * | 1/2001 | Luzon | ........................... 524/284 |
| 7,022,750 B2 | 4/2006 | Camp et al. | |
| 7,211,173 B1 | 5/2007 | Staerzl et | |

(Continued)

FOREIGN PATENT DOCUMENTS

CN 101533122 A 9/2009
EP 0465172 A1 1/1992

(Continued)

OTHER PUBLICATIONS

P. J. Baum, Go-Faster Strips, Stripes, Riblets, etc.: Speedskating Drag Reduction and the 'Lost Dutchman Olympic Gold Mine' Speedskating Santa Barbara, Feb. 14, 1998.

(Continued)

*Primary Examiner* — Isam Alsomiri
*Assistant Examiner* — Hovhannes Baghdasaryan

(57) ABSTRACT

Systems and methods comprise marine geophysical equipment with polyurethane-based material at least partially covering a surface. The surface also at least partially coated with a suspension medium and with a biocide. A method comprises disposing such marine geophysical equipment in a body of water. A method comprises applying a suspension medium and a biocide to a surface at least partially covered with a polyurethane-based material.

20 Claims, 4 Drawing Sheets

(56) References Cited

U.S. PATENT DOCUMENTS

| | | |
|---|---|---|
| 7,487,840 B2 | 2/2009 | Gammage et al. |
| 7,835,222 B2 | 11/2010 | Lobe et al. |
| 8,091,647 B2 | 1/2012 | Nicholson |
| 2006/0002234 A1 | 1/2006 | Lobe et al. |
| 2006/0090593 A1 | 5/2006 | Liu |
| 2006/0144286 A1 | 7/2006 | Baum |
| 2006/0203613 A1 | 9/2006 | Thomsen et al. |
| 2007/0213426 A1 | 9/2007 | Abou-Nemeh |
| 2008/0192569 A1 | 8/2008 | Ray et al. |
| 2009/0097356 A1 | 4/2009 | Haldorsen et al. |
| 2009/0159204 A1* | 6/2009 | Burckhardt .............. 156/331.1 |
| 2009/0238811 A1* | 9/2009 | McDaniel et al. .......... 424/94.2 |
| 2010/0020644 A1 | 1/2010 | Vignaux |
| 2010/0108813 A1 | 5/2010 | Lang |
| 2010/0269731 A1 | 10/2010 | Tofte Jespersen et al. |
| 2010/0278011 A1 | 11/2010 | Harrick |
| 2010/0278771 A1 | 11/2010 | Lobe et al. |
| 2011/0123477 A1 | 5/2011 | Mount et al. |
| 2011/0174207 A1 | 7/2011 | Harrick et al. |
| 2011/0255369 A1 | 10/2011 | Harrick et al. |
| 2011/0311769 A1 | 12/2011 | Chen et al. |
| 2012/0205246 A1 | 8/2012 | Chew |
| 2012/0243370 A1 | 9/2012 | Vignaux |
| 2012/0250458 A1 | 10/2012 | Tonchia |
| 2012/0301423 A1 | 11/2012 | Chai et al. |
| 2012/0321809 A1 | 12/2012 | Hartshorne et al. |
| 2013/0039153 A1 | 2/2013 | Hartshorne et al. |
| 2013/0142013 A1* | 6/2013 | Hartshorne et al. .......... 367/153 |

FOREIGN PATENT DOCUMENTS

| | | |
|---|---|---|
| EP | 2348078 A1 | 7/2011 |
| GB | 2246723 A | 2/1992 |
| GB | 2394479 B | 5/2005 |
| JP | 2005034770 A | 2/2005 |
| JP | 2007169449 A | 7/2007 |
| WO | 8910947 A1 | 11/1989 |
| WO | 2008121418 A1 | 10/2008 |
| WO | 2011070411 A2 | 6/2011 |

OTHER PUBLICATIONS

D.W. Bechert, M. Bruse, W. Hage, R. Meyer, Fluid Mechanics of Biological Surfaces and Their Technological Application, Springer-Verlag 2000.

J. Karthikeyan, Cold Spray Technology: International Status and USA Efforts, Barberton, Ohio, USA, ASB Industries Inc., Dec. 2004.

NASA Riblets for Stars & Stripes, Fact Sheets, www.nasa.gov, Oct. 1993.

Martha J. Heil, Shark-Inspired Boat Surface Materials Engineers Turn to Ferocious Fish for Nonstick Ship Coating, American Institute of Physics, www.aip.org, May 1, 2005.

William H. Dresher, PH. D., Copper in Third-Generation Antifoulants for Marine Coatings, www.copper.org, 1-4.

Combined Search and Examination Report issued by the United Kingdom Intellectual Property Office for patent application No. GB1404971.2, mailed Apr. 23, 2014, 5 pages.

English Abstract of Japanese application No. JP2005034770 from the EPODOC, EPO and WPI,Thompson, publication date: Feb. 10, 2005, 1 page.

United Kingdom Search Report for Application No. GB1200345.5, dated: Apr. 10, 2012.

Matic, Jake, Patent Examination Report No. 1, Oct. 14, 2013, IP Australia (Australian Government), Australia.

Goacher, Laura, Patents Act 1977: Examination Report under Section 18(3), Nov. 26, 2013, Intellectual Property Office, United Kingdom.

Combined Search and Examination Report issued by the United Kingdom Intellectual Property Office for patent application No. GB1404970.2, mailed Apr. 29, 2014, 6 pages.

English Abstract of Japanese application No. JP2007169449 from the EPODOC, EPO and WPI,Thompson, publication date: Jul. 5, 2007, 2 pages.

English Abstract of Chinese application No. CN101533122 from the EPODOC, EPO and WPI,Thompson, publication date: Sep. 16, 2009, 2 pages.

* cited by examiner

SYSTEM AND METHOD FOR USING BIOCIDE COATING TO PREVENT MARINE GROWTH ON GEOPHYSICAL EQUIPMENT

CROSS-REFERENCE TO RELATED APPLICATIONS

This application claims the benefit of U.S. Provisional Application No. 61/460,962, entitled "System and Method for Using Biocide Coating to Prevent Marine Growth on Geophysical Equipment," filed Jan. 11, 2011, the entire disclosure of which is incorporated herein by reference.

STATEMENT REGARDING FEDERALLY SPONSORED RESEARCH OR DEVELOPMENT

Not applicable.

BACKGROUND OF THE INVENTION

This invention relates generally to the field of geophysical prospecting. More particularly, the invention relates to the field of cables and equipment for marine geophysical surveys.

In the oil and gas industry, geophysical prospecting is commonly used to aid in the search for and evaluation of subterranean formations. Geophysical prospecting techniques yield knowledge of the subsurface structure of the earth, which is useful for finding and extracting valuable mineral resources, particularly hydrocarbon deposits such as oil and natural gas. A well-known technique of geophysical prospecting is a seismic survey.

Marine geophysical surveying, such as seismic or electromagnetic surveying, is typically performed using sensor cables, such as "streamers" towed near the surface of a body of water or an "ocean bottom cable" or "node" disposed at or near the water bottom. A streamer is in the most general sense a cable towed by a vessel. The sensor cable has a plurality of sensors disposed thereon at spaced apart locations along the length of the cable. In the case of marine seismic surveying the sensors are typically hydrophones, but can also be any type of sensor that is responsive to the pressure in the water, or in changes therein with respect to time or may be any type of particle motion sensor, such as a velocity sensor or an acceleration sensor, known in the art. In the case of marine electromagnetic surveying, the sensors may be electrodes or magnetic field sensors. Irrespective of the type of such sensors, the sensors typically generate an electrical or optical signal that is related to the parameter being measured by the sensors. The electrical or optical signals are conducted along electrical conductors or optical fibers carried by the streamer to a recording system. The recording system is typically disposed on the vessel, but may be disposed elsewhere.

Unfortunately, marine organisms adhere to and then grow on nearly everything that is placed in water for significant periods of time, including towed or ocean bottom geophysical equipment. Marine growth is often pictured in terms of barnacles, but also includes the growth of mussels, oysters, algae, bacteria, tubeworms, slime, and other marine organisms.

Marine growth results in lost production time required to clean the geophysical equipment. In addition, marine growth speeds corrosion, requiring quicker replacement of equipment, and increases drag resistance, leading to increased fuel costs. Thus, the elimination, or the reduction, of marine growth will have a major beneficial effect on the cost of marine geophysical surveying. Hence, marine growth presents a significant problem for a geophysical vessel operation due to downtime caused by a need for its removal, equipment damage, reduced seismic data quality due to increased noise, increased fuel consumption, and exposure of the crew to dangers associated with a streamer cleaning operations.

Thus, a need exists for a system and a method for protecting geophysical equipment in marine geophysical surveys, especially sensor cables, from marine growth.

BRIEF DESCRIPTION OF THE DRAWINGS

The invention and its advantages may be more easily understood by reference to the following detailed description and the attached drawings, in which.

Figure 1:
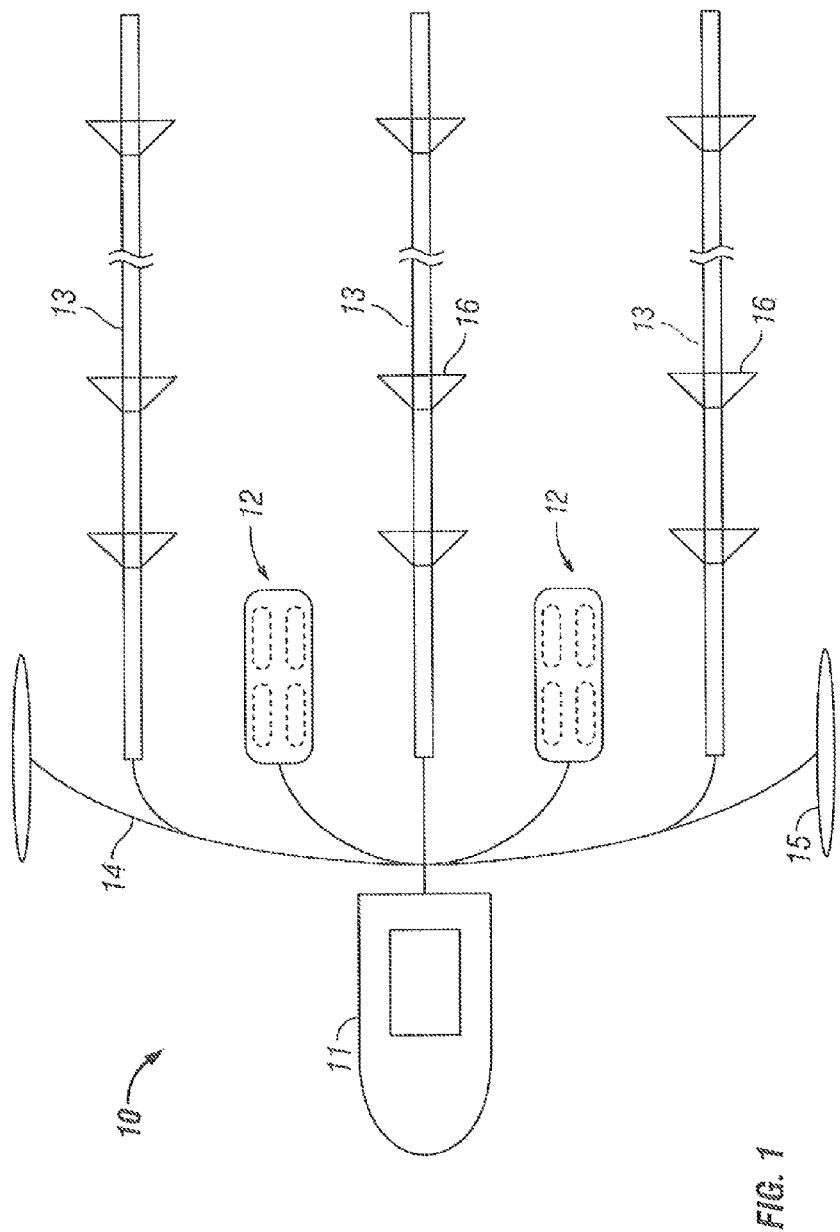
FIG. 1 is a schematic plan view of marine geophysical survey equipment used with towed seismic streamers.

While the invention will be described in connection with its preferred embodiments, it will be understood that the invention is not limited to these. On the contrary, the invention is intended to cover all alternatives, modifications, and equivalents that may be included within the scope of the invention, as defined by the appended claims.

DETAILED DESCRIPTION

Marine growth is a problem for anything that is submerged in or moves through sea water for significant periods of time, including marine geophysical equipment. Thus, it is desirable to affix materials with biocide properties ("biocides") to the surfaces of marine geophysical equipment. In particular, it is well-known in the art that copper has anti-fouling properties against marine growth when submerged in sea water.

The invention amongst various embodiments a system and a method for protecting marine geophysical equipment from marine growth. The following discussion of embodiments of the invention will be illustrated in terms of surface jackets of sensor cables, but this is not a limitation of the invention. Any form of geophysical equipment that can be or is disposed in a body of water is vulnerable to marine growth. Likewise, any such equipment with a polyurethane-based outer covering is considered appropriate for application of the present invention. For example, the invention can be applied to lead-ins covered with polyurethane-based materials. Further example, the invention can be applied to sensor cables carrying electromagnetic receivers.

In one embodiment, the invention includes a system and method for application of a coating comprising a mixture of suspension medium and biocide to surfaces of geophysical equipment components covered by polyurethane-based materials. The biocide coating may greatly reduce or perhaps even eliminate problems associated with marine growth.

In one particular embodiment, the biocide comprises particles of copper or particles of an alloy containing a significant amount of copper. Copper alloys include, but are not limited to, brass, copper oxide, copper thiocyanate, copper bronze, copper napthenate, copper resinate, copper nickel, and copper sulfide.

An embodiment of the invention comprises applying the biocide suspended in a suspension medium to the outer surface of a polyurethane surface jacket. The suspension medium is chosen so that it reacts with the polyurethane material and causes it to become "tacky". Then, the biocide adheres to the surface jacket surface. In a particular embodiment of the invention, the biocide comprises copper or copper alloy particles. In another embodiment, the biocide comprises a combination of copper or copper alloy particles and other biocide materials. In some embodiments, the suspension medium is a dissolved polyurethane. For example, the suspension medium may be a mixture of N-Methyl-2-pyrrolidone ("NMP") and polyurethane. As would be appreciated by one of ordinary skill in the art with the benefit of this disclosure, the suspension medium may exhibit a viscosity high enough to allow the biocide particles to remain in suspension, while also interacting with the surfaces of the geophysical equipment to create an adherence between the biocide particles and the geophysical equipment.

One important consideration is to limit the penetration of the suspension medium into the polyurethane by stopping further reaction of the suspension medium with the polyurethane, and thus preventing irreversible damage to the polyurethane surface. Also, a short curing time, brought about by stopping the reaction, allows the treated streamer surface jacket of the sensor cables to be handled quickly and stored on a storage reel. Consequently, a curing agent may be applied to the geophysical equipment. For example, applying water (or a water-based liquid, gel, or foam) to a polyurethane surface treated with the mixture of suspension medium and biocide in a form of a stream or a mist causes the suspension medium to cure, substantially instantly, and form a well-bonded film that contains the biocide. In another embodiment, the biocide, especially if in the form of particles, can be applied (blown, sprinkled) to a surface that is "wetted" with the suspension medium or can be sprayed or brushed as a mixture of suspension medium and biocide. In yet another embodiment, the suspension medium may comprise a solvent, such as NMP, diluted with another less-aggressive solvent to prevent over-reaction with the polyurethane-based coating material, especially when the temperature is hotter.

It may be desired to increase the thickness of the film of suspension medium and biocide created and to improve biocide suspension in the mixture. In this case, the viscosity of the suspension medium can be adjusted by dissolving a defined amount of virgin polyurethane material in the suspension medium. Such a mixture can be than brushed, rolled or sprayed over a surface jacket's outer surface, allowing for automation of the process.

Figure 2:
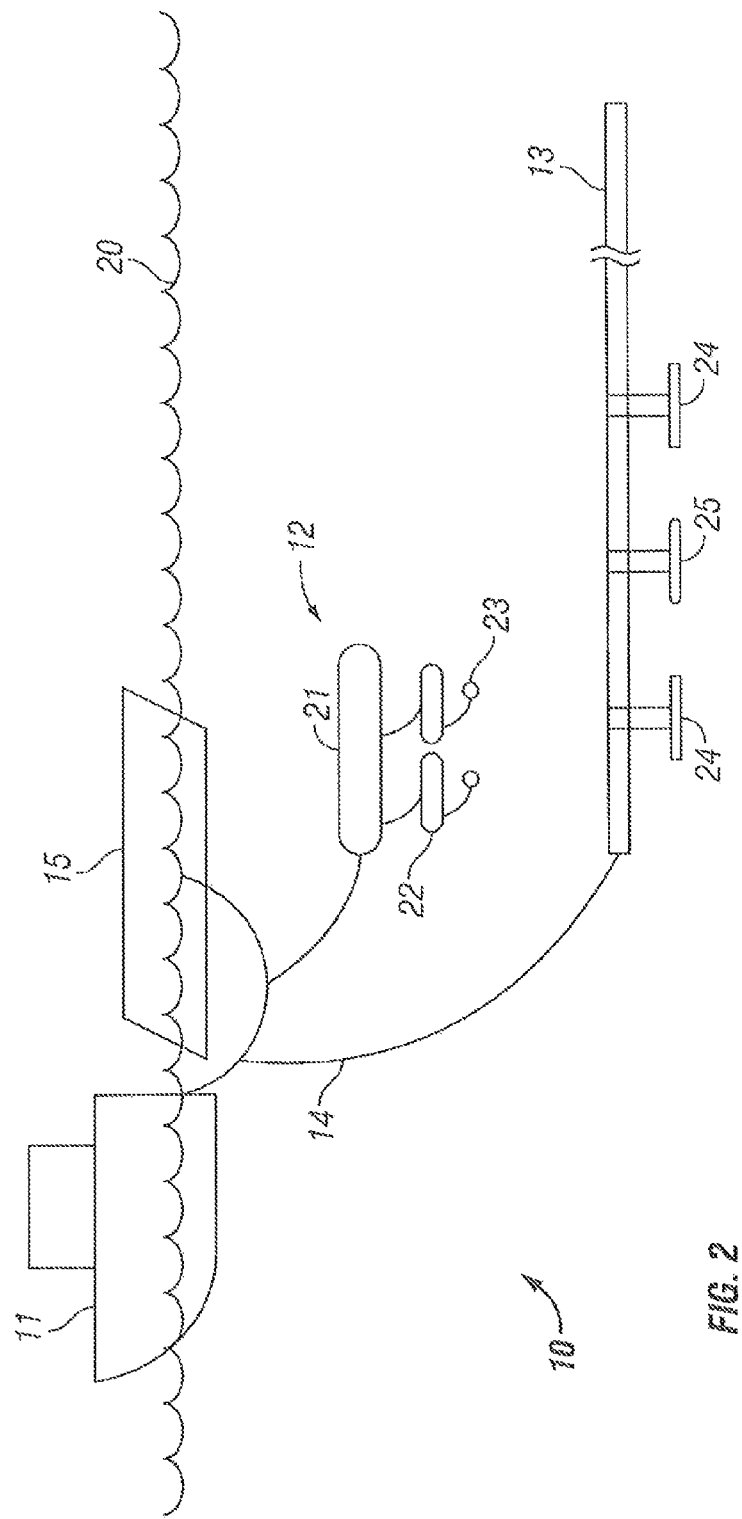
FIG. 2 is a schematic side view of marine geophysical survey equipment used with towed seismic streamers.

FIGS. 1 and 2 show the exemplary types of marine geophysical equipment that can be protected from marine growth by various embodiments of the apparatus and method of the invention. As already discussed, the invention is not limited to towed seismic streamers, which are only employed here in the figures for illustrative purposes. FIG. 1 is a schematic plan view (not drawn to scale) of marine geophysical survey equipment that could be used with towed seismic streamers.

The marine seismic equipment is generally designated by reference numeral 10. A seismic vessel 11 tows seismic sources 12 and seismic streamers 13. Although only two seismic sources 12 and three seismic streamers 13 are shown, this number is just for illustrative purposes only. Typically, there can be more seismic sources 12 and many more seismic streamers 13. The seismic sources 12 and the seismic streamers 13 are connected to the seismic vessel 11 by cables (lead-ins) 14. The cables 14 are typically further connected to devices such as deflectors 15 that spread apart the seismic streamers 13. FIG. 1 shows that the seismic streamers 13 may have equipment attached inline or around the streamers 13.

The attached equipment can be, by way of example, in-line mounted position control devices 16, such as depth control devices or lateral control devices, as well as acoustic units and retriever units (not shown). The attached equipment also can be, by way of example, sensors of various types, such as depth sensors.

FIG. 2 is a schematic side view (not drawn to scale) of marine geophysical survey equipment, including towed seismic streamers. The side view in FIG. 2 corresponds to the plan view of the marine seismic equipment shown in FIG. 1.

The seismic vessel 11 tows seismic sources 12 and seismic streamers 13 under the water surface 20. The seismic sources 12 primarily comprise floats 21 and air guns 22, but may also have equipment such as, for example, near-field sensors (hydrophones) 23 attached adjacent the air guns 22. FIG. 2 shows that the seismic streamers 13 may have additional equipment attached below the streamers 13. The attached equipment can be, by way of example, suspended position control devices 24 and suspended sensors 25, as well as acoustic units and retriever units (not shown).

Figure 3:
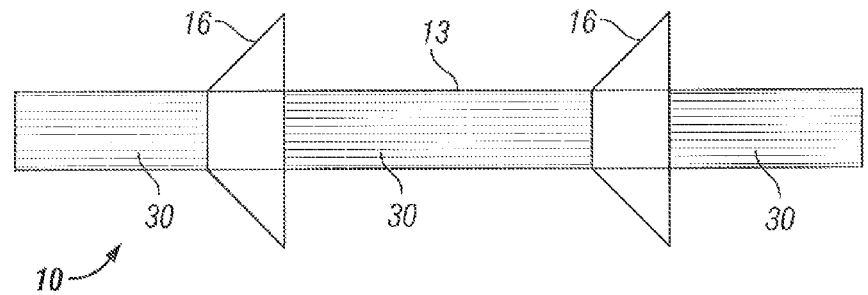
FIG. 3 is a schematic plan view of a seismic streamer, protected from marine growth by the invention.
Figure 4:
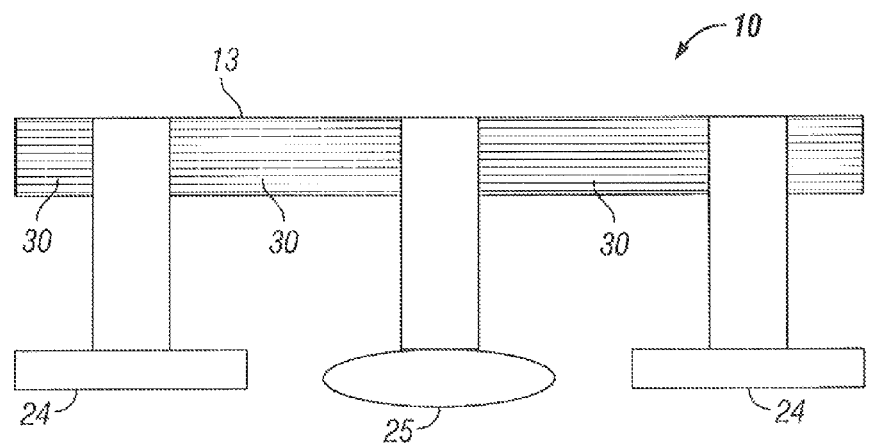
FIG. 4 is a schematic side view of a seismic streamer, protected from marine growth by the invention.

FIGS. 3 and 4 show close-up views of the seismic equipment attached to the seismic streamer in FIGS. 1 and 2, respectively. FIG. 3 is a schematic plan view (not drawn to scale) of a seismic streamer, protected from marine growth by the invention.

A coating 30, comprising a mixture of suspension medium and biocide, covers portions of the towed marine seismic equipment 10 that is covered by polyurethane-base outer covers. In one embodiment, the coating 30 of a mixture of suspension medium and biocide is shown covering a portion of the seismic streamer 13. The coating 30 shown here in FIGS. 3 and 4 is for illustrative purposes only and are not meant to limit the invention. The coating 30 could also, for example, cover a towed marine streamer used for electromagnetic surveying, an ocean bottom cable or a lead-in. The coating 30 of the invention can be applied to cover any portion of the marine seismic equipment 10 that is covered by a polyurethane-based outer covering.

FIG. 4 is a schematic side view (not drawn to scale) of a seismic streamer, protected from marine growth by the invention. As in FIG. 3 above, the coating 30 of the mixture of suspension medium and biocide is shown covering the surface jacket of the towed seismic streamer 13.

Figure 5:
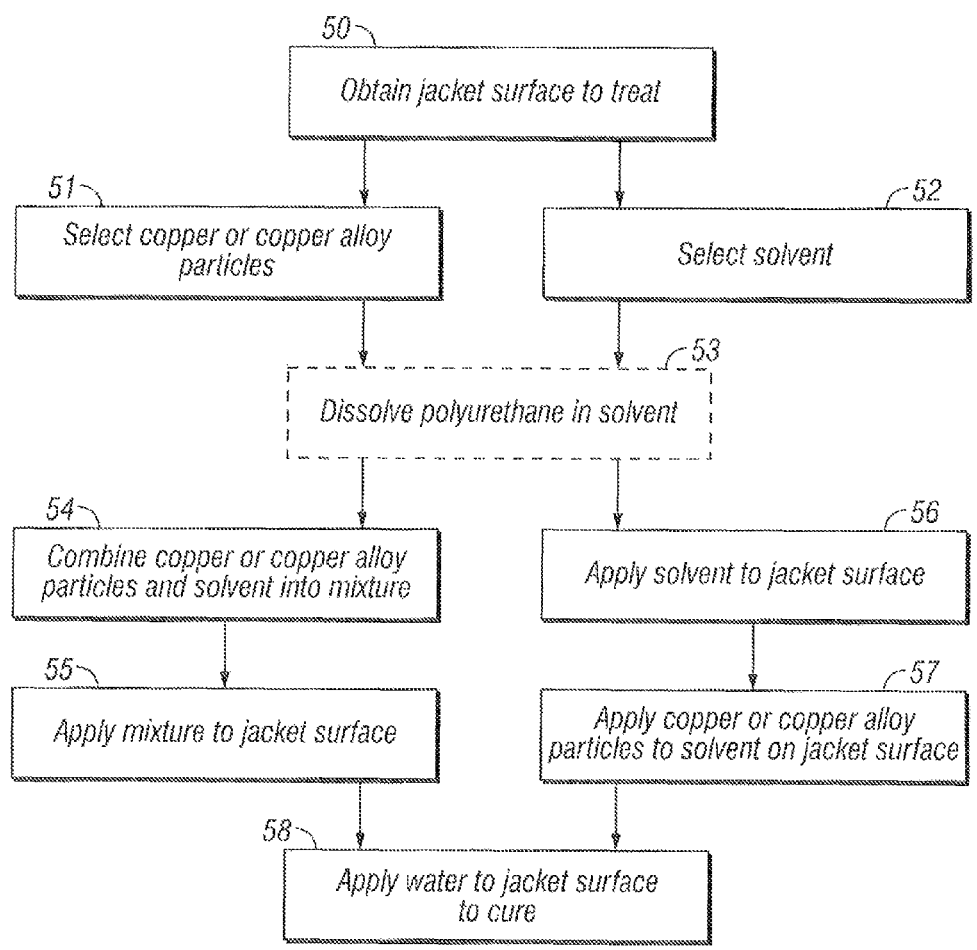
FIG. 5 is a flowchart showing an embodiment of the method of the invention for protecting marine geophysical equipment from marine growth.

FIG. 5 is a flowchart showing an embodiment of the method of the invention for protecting marine geophysical equipment from marine growth. The invention is here illustrated with the embodiment utilizing copper or copper alloy particles as the biocide. This is not intended to limit the invention, in which other materials that have biocide qualities can be employed or included with the copper or copper alloys. The invention is here illustrated with an embodiment applied to a surface jacket. This is not intended to limit the invention, which can be applied to any surface that is covered by a polyurethane-based material.

At block 50, a surface jacket is obtained. The surface jacket is the outer protective covering of marine geophysical equipment, such as an ocean bottom cable or a towed seismic or electromagnetic streamer. The surface jacket comprises or, at least, is covered by a polyurethane-based material. In one embodiment, the surface jacket comprises polyurethane.

At block 51, copper or copper alloy particles are selected. The copper or copper alloy particles comprise particles of copper or particles of copper alloys containing a significant amount of copper. Again, the selection of copper or copper alloy particles is intended for illustrative purposes only, and is not intended to limit the selection of biocide.

At block 52, a suspension medium is selected. The suspension medium is selected to react with the surface jacket obtained in block 50 to make the surface jacket tacky enough to hold the copper or copper alloy particles selected in block 51. In one embodiment, the suspension medium is NMP. In another embodiment, the NMP is diluted with another less-aggressive solvent to prevent over-reaction with the polyurethane-based coating material. One of ordinary skill in the art with the benefit of this disclosure will be capable of selecting an appropriate suspension medium for the intended operating conditions.

At block 53, optionally, virgin polyurethane material is dissolved in the suspension medium selected in block 52. This will increase the viscosity of the suspension medium before the copper or copper alloy particles are combined with the suspension medium in either block 54 or 57, below. This will increase the thickness of the film of suspension medium and copper or copper alloy particles created and improve copper particle suspension in the mixture. Such a mixture can be than brushed, rolled, or sprayed over a surface jacket's outer surface, allowing for automation of the process. Then, the process proceeds to either block 54 or 56.

At block 54, the copper or copper alloy particles selected in block 51 and the suspension medium selected in block 52 are combined into a mixture.

At block 55, the mixture combined in block 54 is applied to the surface jacket surface obtained in block 50. Then, the process proceeds to block 58.

At block 56, the suspension medium selected in block 52 is applied to the surface jacket surface obtained in block 50.

At block 57, the copper or copper alloy particles selected in block 51 are applied to the surface jacket surface obtained in block 50.

At block 58, water as a curing agent is applied to the surface jacket surface obtained in block 50. Applying water (or a water-based liquid, gel, or foam) to a polyurethane surface treated with the suspension medium and copper or copper alloy particles mixture causes the suspension medium to cure, substantially instantly. This forms a well-bonded film that contains and secures the copper or copper alloy particles. The water can be applied, for example, in the form of a stream or a mist. Additionally, curing the suspension medium allows the streamer surface jacket or completed streamer section to be handled quickly and stored on a storage reel. Again, the selection of water (or a water-based liquid, gel, or foam) as a curing agent is intended for illustrative purposes only, and is not intended to limit the selection of curing agent.

The above process described in FIG. 5 needs to be controlled, to prevent permanent damage to the substrate, the polyurethane-based coating material. Factors that need to be controlled include, but are not limited to, the concentration of the suspension medium (NMP and others), the quantity of suspension medium and the biocide, such as the copper or copper alloy particles illustrated, application conditions such as temperature, and time between application of the suspension medium and the curing treatment. One of ordinary skill in the art with the benefit of this disclosure will be capable of selecting appropriate factors for the intended operating conditions.

The biocide coating of the invention may prevent settlement of the invertebrate larvae (macro-fouling), algae, and bacteria (micro-fouling) that cause marine growth. Thus, in one system and method of the invention, depositing biocide onto polyurethane-based material surfaces of geophysical equipment, such as surface jackets of sensor cables, may prevent or reduce invertebrate, algae, and bacteria settlement.

Reduction of marine growth on marine geophysical equipment will result in several advantages, including the following.

The reduction of marine growth may reduce eddy formation at the surfaces of the geophysical equipment, bringing about a consequent reduction of noise caused by the turbulent flow. The quieter towing may improve the signal-to-noise ratio, a great benefit in geophysical surveying.

The reduction of marine growth may reduce drag on a towed streamer, allowing the equipment to be towed through the water with higher energy efficiency. This higher efficiency could produce a reduction in fuel costs for the same survey configuration. Alternatively, the higher efficiency could allow greater towing capacity (such as an increase in the number of streamers, the length of each streamer, or the towing spread) at the current fuel costs and towing power of the seismic vessel.

The reduction of marine growth may reduce production time lost to cleaning or replacing geophysical equipment. This may also reduce work boat and cleaning equipment exposure hours for the crew. The reduction of marine growth may reduce the wear and extend the operational life of the geophysical equipment.

In the system and method of the invention, biocide density may be adjusted to produce a protective coating that provides the advantages discussed above and, at the same time, is suitable for the seismic or electromagnetic cable application. In a particular embodiment, a copper or copper alloy coating may be selected to not be so thick or contain so much copper as to interfere with the acoustic properties of sensors in the streamers, such as hydrophones and geophones, or the properties of electromagnetic sensors.

It should be understood that the preceding is merely a detailed description of specific embodiments of this invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents.

We claim:

1. A system, comprising:
a marine geophysical equipment;
a polyurethane-based material at least partially covering a surface of the marine geophysical equipment; and
a suspension medium and a biocide at least partially coating the covered surface, wherein the biocide is adhered to the polyurethane-based material by a reaction of the suspension medium with the polyurethane-based material causing the polyurethane-based material to become tacky.

2. The system of claim 1, wherein the surface comprises a surface jacket of a sensor cable.

3. The system of claim 2, wherein the sensor cable comprises at least one cable selected from the group consisting of: a towed marine seismic streamer, a towed marine electromagnetic streamer, an ocean bottom seismic cable, an ocean bottom electromagnetic cable, and any combination thereof.

4. The system of claim 1, wherein the biocide comprises copper or copper alloy particles.

5. The system of claim 1, wherein the suspension medium comprises N-Methyl-2-pyrrolidone.

6. A method for protecting marine geophysical equipment from marine growth, comprising:
at least partially covering a surface of the marine geophysical equipment with a polyurethane-based material; and at least partially coating the covered surface with a suspension medium and with a biocide, wherein the suspension medium reacts with the polyurethane-based material to material to cause the polyurethane-based material to become tacky such that the biocide adheres to the polyurethane-based material.

7. The method of claim 6, further comprising applying a curing agent to the coated and covered surface.

8. The method of claim 7, wherein the curing agent is water.

9. The method of claim 6, wherein the surface comprises a surface jacket of a sensor cable.

10. The method of claim 9, wherein the sensor cable comprises at least one cable selected from the group consisting of: a towed marine seismic streamer, a towed marine electromagnetic streamer, an ocean bottom seismic cable, an ocean bottom electromagnetic cable, and any combination thereof.

11. The method of claim 6, wherein the at least partially coating the covered surface comprises:
  combining the suspension medium and the biocide into a mixture; and
  applying the mixture to the covered surface.

12. The method of claim 11, wherein the mixture further comprises a polyurethane material.

13. The method of claim 6, wherein the at least partially coating the covered surface comprises:
  applying the suspension medium to the covered surface to create a suspension medium-coated surface; and
  applying the biocide to the suspension medium-coated surface.

14. The method of claim 6, wherein the biocide comprises copper or copper alloy particles.

15. The method of claim 6, wherein the suspension medium comprises N-Methyl-2-pyrrolidone.

16. A method of geophysical surveying comprising:
  selecting marine geophysical equipment comprising:
    a polyurethane-based material at least partially covering a surface of the marine geophysical equipment; and
    a suspension medium and a biocide at least partially coating the covered surface, wherein the biocide is adhered to the polyurethane-based material by a reaction of the suspension material with the polyurethane-based material causing the polyurethane-based material to become tacky; and
  disposing the marine geophysical equipment in a body of water.

17. The method of claim 16, wherein the surface comprises a surface jacket of a sensor cable.

18. The method of claim 17, wherein the sensor cable comprises at least one cable selected from the group consisting of: a towed marine seismic streamer, a towed marine electromagnetic streamer, an ocean bottom seismic cable, an ocean bottom electromagnetic cable, and any combination thereof.

19. The method of claim 16, wherein the biocide comprises copper or copper alloy particles.

20. The method of claim 16, wherein the suspension medium comprises N-Methyl-2-pyrrolidone.

* * * * *